(12) United States Patent
Lim et al.

(10) Patent No.: US 6,196,967 B1
(45) Date of Patent: Mar. 6, 2001

(54) ARTHROSCOPIC COMPONENT JOINING SYSTEM

(75) Inventors: Joepert R. Lim, Palm Harbor; Phillip J. Berman, St. Petersburg, both of FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/271,559

(22) Filed: Mar. 18, 1999

Related U.S. Application Data
(60) Provisional application No. 60/078,484, filed on Mar. 18, 1998.

(51) Int. Cl.[7] .................................................. A61B 1/00
(52) U.S. Cl. ..................... 600/125; 604/164.07; 604/538
(58) Field of Search ................... 604/164.07, 165.01, 604/165.02, 165.03, 165.04, 538, 533, 534, 264; 600/121, 124, 125

(56) References Cited

U.S. PATENT DOCUMENTS

| | | |
|---|---|---|
| 4,252,122 | 2/1981 | Halvorsen . |
| 4,254,762 | 3/1981 | Yoon . |
| 4,610,242 | 9/1986 | Santangelo et al. . |
| 4,769,018 | 9/1988 | Wilson . |
| 4,857,062 | 8/1989 | Russell . |
| 4,951,977 | 8/1990 | Shutt . |
| 5,037,386 | 8/1991 | Marcus et al. . |
| 5,087,080 | 2/1992 | Shutt . |
| 5,209,219 | 5/1993 | Hollobaugh . |
| 5,261,888 | 11/1993 | Semm . |
| 5,290,294 | 3/1994 | Cox et al. . |
| 5,383,860 | 1/1995 | Lau . |
| 5,456,673 | 10/1995 | Ziegler et al. . |
| 5,954,708 * | 9/1999 | Lopez et al. ..................... 604/533 |

* cited by examiner

Primary Examiner—Michael H. Thaler
(74) Attorney, Agent, or Firm—Gene Warzecha

(57) ABSTRACT

An arthroscopic or endoscopic component joining system for selectively and temporarily connecting instruments during closed surgical procedures. The system is modular and operable as a bridge system for connecting instruments to selected cannulas or as a sheath system for connecting a scope to a scope sheath. Various improvements provide for greater fluid flow through the components than is available with known systems of similar size.

11 Claims, 7 Drawing Sheets

ARTHROSCOPIC COMPONENT JOINING SYSTEM

This application claims benefit to Provisional application 60/078,484 filed Mar. 18, 1998.

BACKGROUND OF THE INVENTION

1. Field of the Invention

The invention relates to surgical instruments for performing endoscopic (e.g. arthroscopic) surgical procedures. More particularly, the invention relates to instruments for detachably joining various arthroscopic instruments together.

2. Description of the Prior Art

Arthroscopic, or more generally, endoscopic surgery is performed by the manipulation of various elongated instruments inserted through natural body openings or portals created to access a surgical site. This is sometimes also referred to as "closed" surgery. The instruments may be, for example, arthroscopes, powered shavers or other cutters, manual instruments, etc. and they may be inserted directly through the opening or portal, or they may be inserted through a cannula. The instruments may in certain instances be temporarily connected or locked to the cannula and, from time to time during a procedure, a surgeon may desire to move an instrument from one cannula to another. Consequently, bridge systems have been developed to facilitate these movements and temporary connections. It has been found, however, that prior art bridge systems could be improved upon with respect to their locking and, in the case of arthroscopic procedures, fluid flow functions and it is an object of this invention to achieve such improvements.

An arthroscopic bridge is a generally cylindrical body having a distal end connectable to a cannula (by, for example, a bayonet type lock) and a proximal end connectable to an obturator or a trocar. Thus, a cannula/bridge/trocar assembly could be created and pushed through a small incision to establish a portal to access a surgical site. The trocar (which could be interchanged with an obturator as well known by those skilled in the art) could then be removed to open the aligned cannula and bridge channels to receive instruments or a scope. However, the known bridge systems have fixed proximal and distal ends that are not modular and do not enable interchangeability of cannula styles (i.e. distal end connections) with various trocar, scope, etc. styles (i.e. proximal end connections). That is, a cannula having a Linvatec/Storz type of connection cannot generally be connected to a scope having another type of connection.

In addition to bridge systems which permit the connection of cannulas to shavers, obturators, trocars, etc., arthroscopic instrumentation may include a sheath system which permits the connection of an arthroscope to a cannulated sheath which receives and protects the scope and its light transmitting optical fibers and provides a channel for communicating irrigating fluid to the work site. (The term "arthroscope" may be used interchangeably with "scope" or "endoscope", and generally refers to an elongated scope for visualizing a surgical site during closed surgical procedures.) A sheath or cannula may also include pressure sensing channels to convey pressure information from the work site. Prior art sheaths often impede fluid flow because of the design of the sheath and/or the design of the connection between the sheath and the scope. Furthermore, prior art sheaths are not known to be suitable for attachment to bridge systems and, therefore, movement of scopes and other instruments among a plurality of cannulas and scope sheaths is somewhat limiting, thereby leading to inefficiencies during closed surgical procedures.

It is accordingly an object of this invention to produce an arthroscopic component joining system for easily and securely joining selected arthroscopic instruments.

It is also an object of this invention to produce a modular arthroscopic component joining system enabling selected joining of arthroscopic components to produce either a bridge system or a sheath system of desired lengths.

As mentioned above, prior art bridge systems and scope sheath systems are also limited in their fluid flow performance. Consequently, it is another object of this invention to provide a system which optimizes fluid flow through the arthroscopic components, such a system being adapted to be either a stand-alone fluid adapter component or a modular component enabling creation of either a bridge system or a sheath system.

SUMMARY OF THE INVENTION

These and other objects are achieved by the preferred embodiment disclosed herein which is an arthroscopic component joining system for joining a first and second body. The system comprises a main body having an axis, a distal end, a proximal end and an axially aligned throughbore. The main body comprises a first connecting means at its proximal end for attachment to the first body (such as a scope, for example) and second connecting means at its distal end for attachment to the second body (such as a scope sheath, for example). The first connecting means comprises a pair of diametrically opposed lever arms, each lever arm pivotably attached to opposing points on the main body and pivotable in a plane common to the lever arms. A common spring means is attached to the lever arms to bias them radially inwardly and a hook edge on each lever arm engages a surface on the second body. The second connecting means comprises a selectively detachable connection means connectable to the second body.

Fluid flow improvements in the preferred embodiment enable greater fluid flow through the various system components than is available in prior art devices of the same diameter. An inclined fluid inlet port opens into a fluid receiving chamber within the main body, the chamber having an open internal structure formed primarily by a plurality of pins holding two spaced annular walls together to define the chamber. A tapered transition between the chamber and an axial flow channel facilitates fluid flow with minimal pressure loss. A scope sheath is connectable to the main body and is provided with a relatively long proximal section and a relatively short distal section. The diameter of the former is larger than the diameter of the latter to minimize pressure losses.

DESCRIPTION OF THE PREFERRED EMBODIMENT

Figure 1:
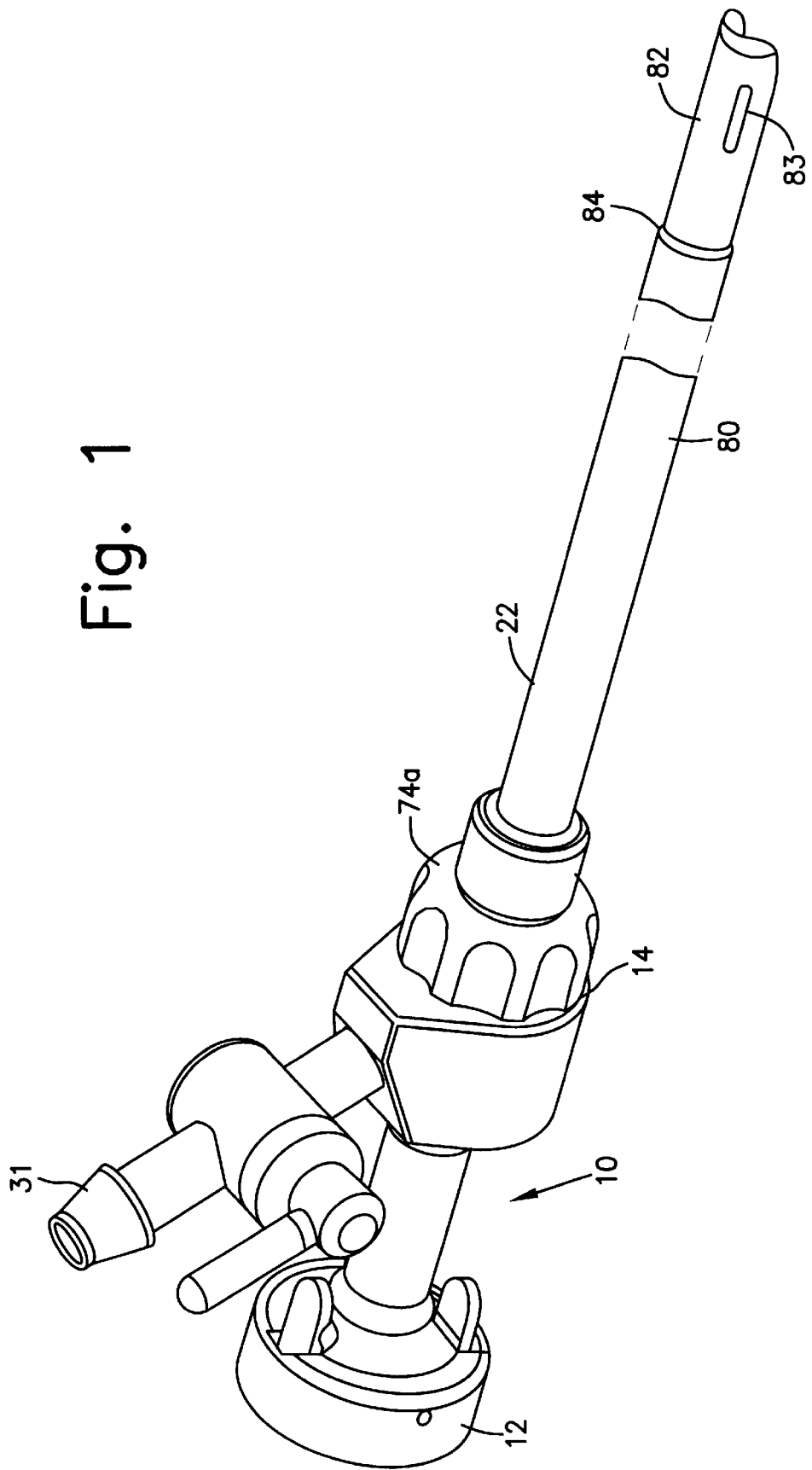
FIG. 1 is a front perspective view of the arthroscopic component joining system configured as a scope sheath system constructed in accordance with the principles of this invention.
Figure 2:
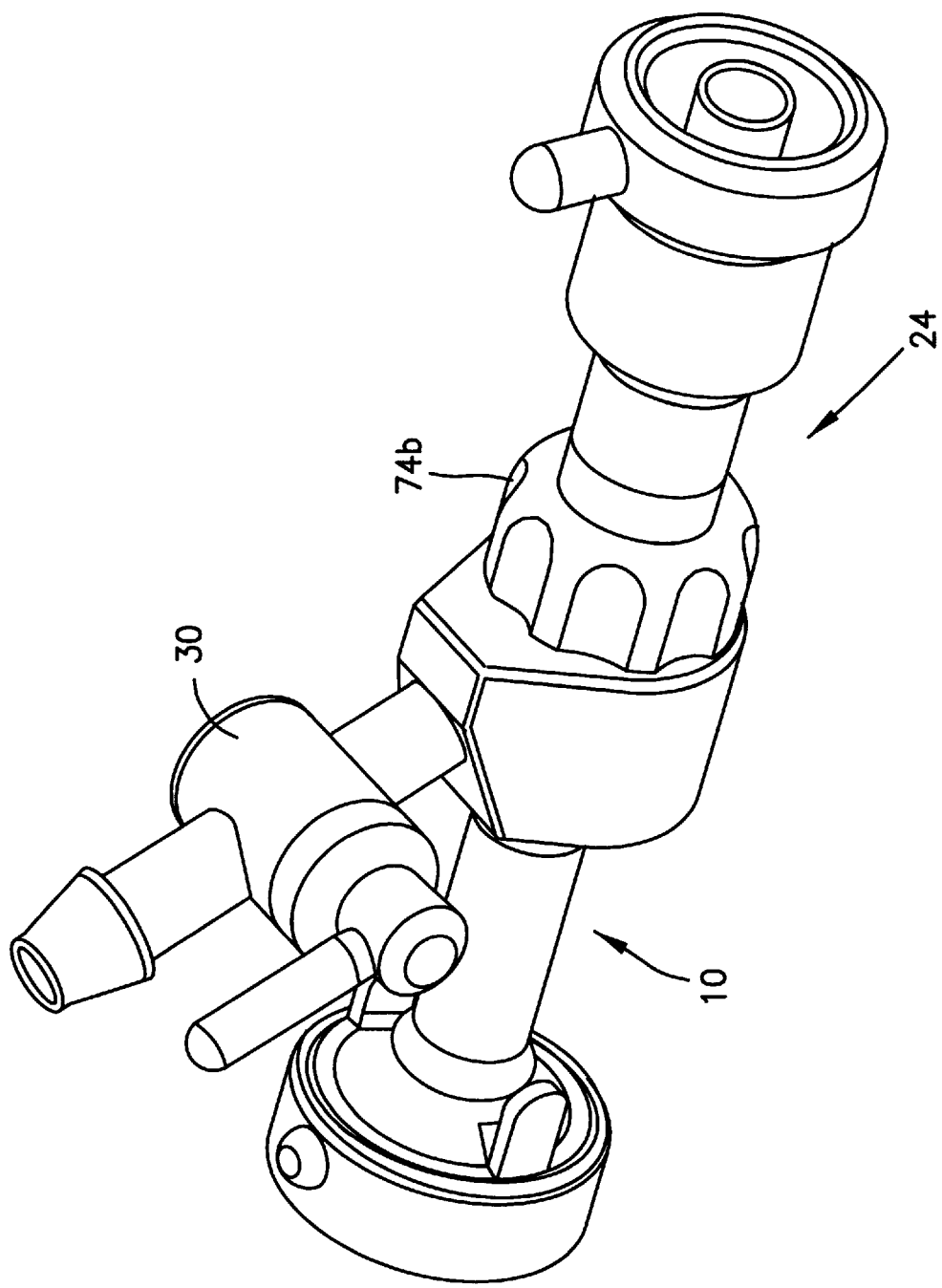
FIG. 2 is a front perspective view of an arthroscopic component joining system configured as a bridge system.

The arthroscopic component joining system shown in FIGS. 1 through 7 is a modular, cannulated system which selectively enables a surgeon to configure the system components into either a sheath configuration as shown in FIG. 1 or a bridge configuration as shown in FIG. 2. The preferred embodiment of the system is designed to receive various arthroscopic instruments and communicate fluid via a tubing set connected to an arthroscopic pump or other fluid source for arthroscopic surgical procedures. It will be understood, however, that the system could be adapted for various other endoscopic procedures as well. As will be explained below, the advantages of the system design are its modularity, high fluid inflow/outflow, low fluid back pressure and improved scope locking mechanism.

Figure 3:
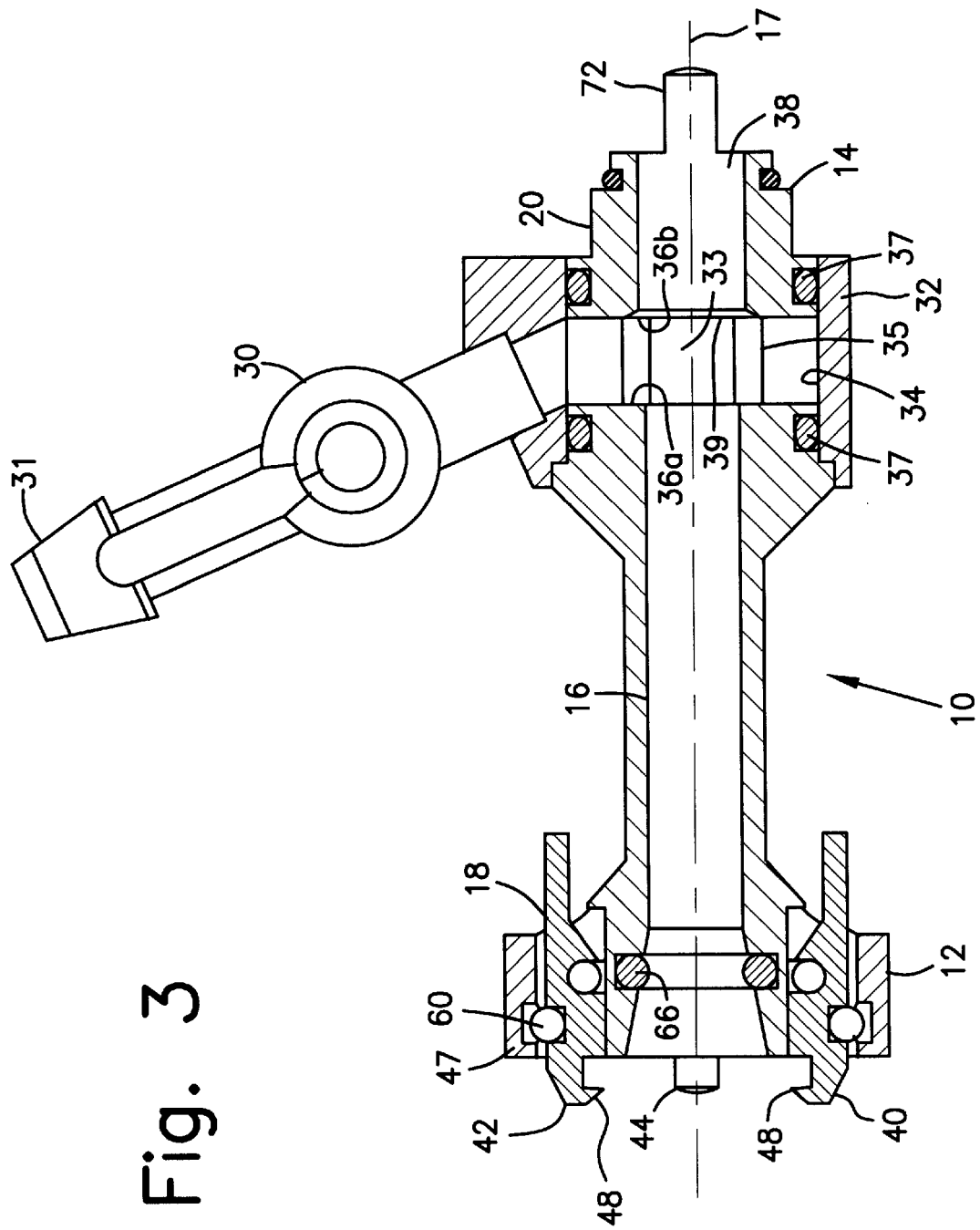
FIG. 3 is a side elevational view partly in cross-section of the main body of the arthroscopic component joining system.

Referring to FIGS. 1–3, the system comprises a main body 10 having a proximal end 12, distal end 14 and a throughbore 16 aligned along axis 17. Proximal end 12 further comprises a selectively releasable locking mechanism 18 for joining main body 10 to an arthroscopic instrument such as scope 54, best seen in FIGS. 5 and 7, as will be further understood below. Distal end 14 further comprises a selectively releasable engagement mechanism 20 for joining main body 10 to an arthroscopic instrument such as, for example, a scope sheath 22, best seen in FIGS. 1 and 5, or a bridge adapter 24, best seen in FIGS. 2 and 6. If a scope sheath is used, it may be directly inserted through a portal. If a bridge adapter is used, it is connectable to a cannula (not shown) so the combined main body/bridge adapter/cannula assembly provides the channel to access the work site. In the preferred embodiment, proximal end 12 is intended to provide a coupling to a conventional Linvatec/Storz type design—one of several different coupling designs known to those skilled in the art. Main body 10 may have a different proximal end 12 adapted to receive a different style coupling and may also have a different coupling mechanism at its distal end 14.

The arthroscopic component joining system is modular in that it can be used in a variety of ways such as, for example, an arthroscopic high inflow scope sheath or an arthroscopic bridge system. Furthermore, the system enables a user to create any one of a variety of sizes (diameters and lengths) and styles of sheaths and bridge/cannula assemblies by carrying in inventory a collection of components rather than complete items. The components may be assembled in any combination. Modularity of this system is possible because of the unique design of the main body 10 which, via the front mount end 20 permits one to create a sheath system by the attachment of the main body to the unique detachable sheath 22 or a bridge system by the attachment of the main body to bridge adapter 24. Other future attachments (not shown) may be feasible as well. Essentially, the main body 10 is analogous to the proximal half of a bridge, thus allowing the distal half to be selected from a variety of components to thereby create a selected instrument (e.g. bridge or sheath).

Figure 4:
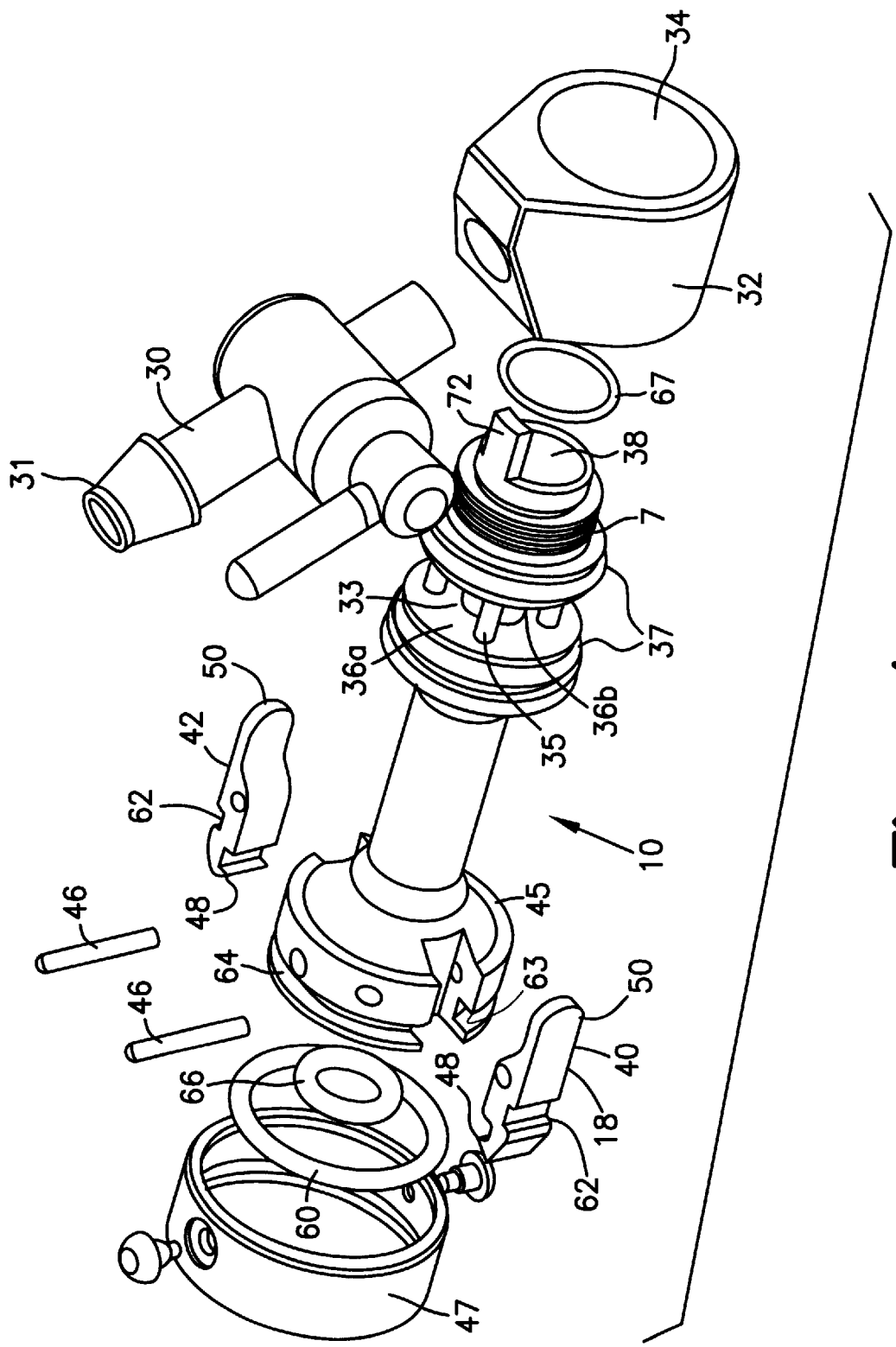
FIG. 4 is an exploded perspective view of the main body shown in FIG. 3.
Figure 5:
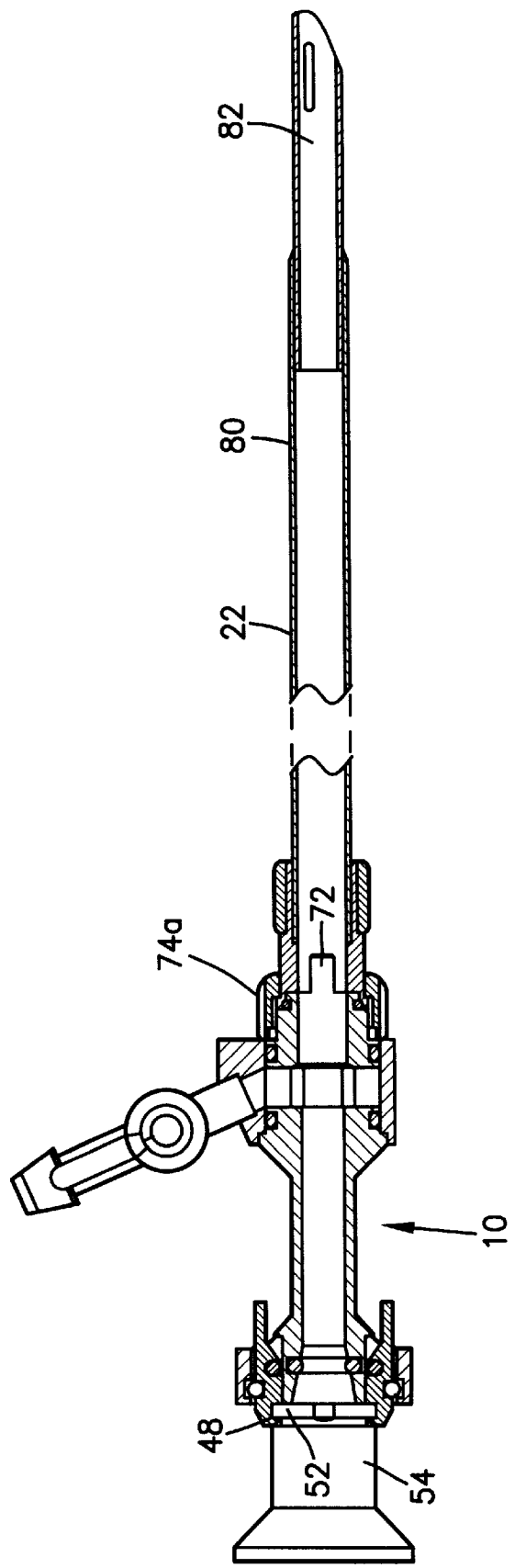
FIG. 5 is a side elevational view partly in cross-section of an arthroscope received within the scope sheath system of FIG. 1.
Figure 7:
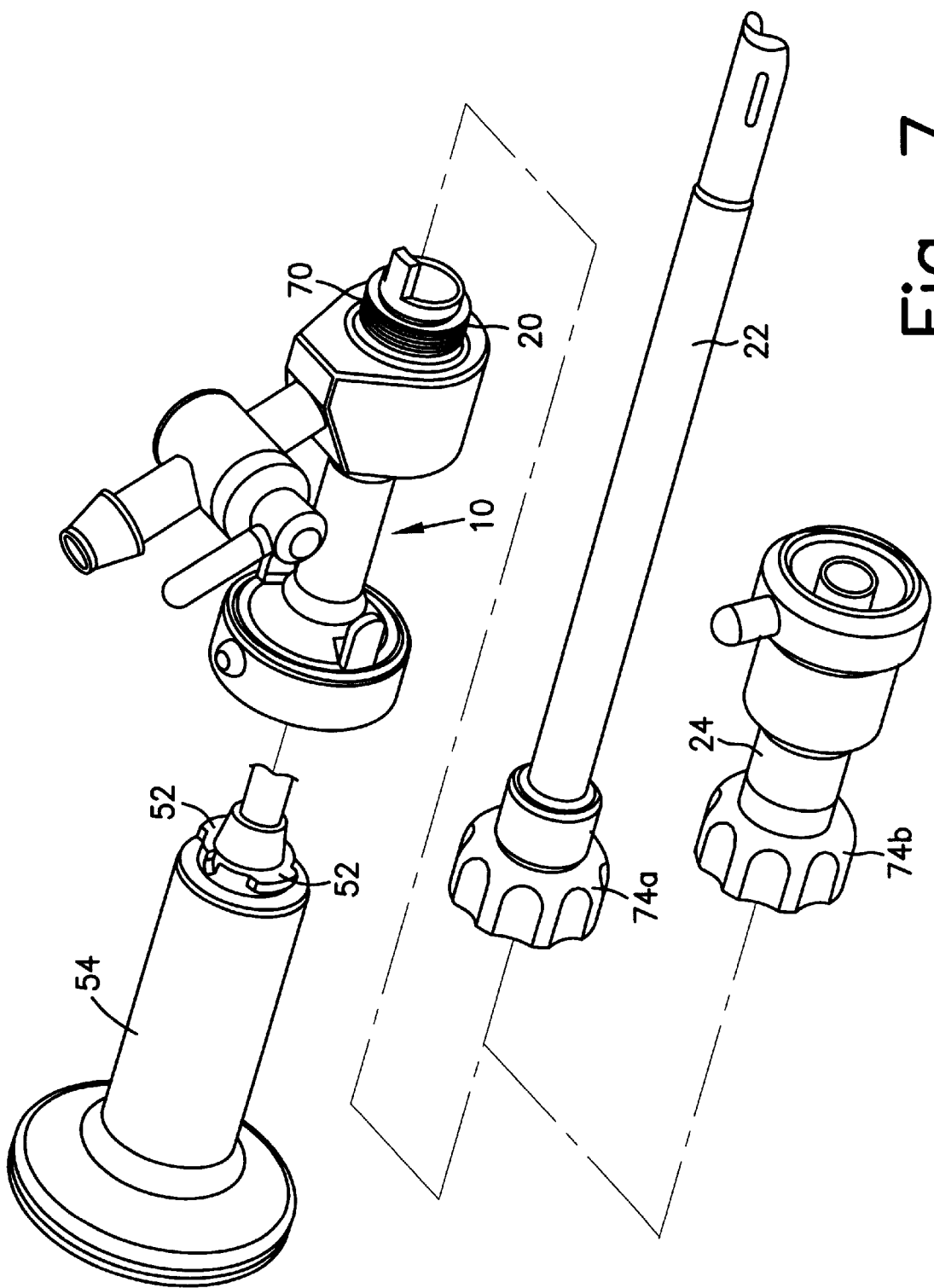
FIG. 7 is a perspective view of the arthroscopic component joining system showing an exploded arrangement of an arthroscope with the main body/sheath assembly or, optionally, with a main body/bridge adapter.

Main body 10 is shown in FIG. 4 in an exploded perspective view. Selective locking mechanism 18 comprises two diametrically opposed spring loaded locking lever arms 40 and 42 and an alignment key 44. Since main body 10 is cylindrical or tubular to accommodate instrument shafts, the locking mechanism 18 is, therefore, essentially mounted on a transverse circular frame 45 made part of the main body. Lever arms 40 and 42 are pivoted about pins 46 and are protected by collar 47 to enable hooks 48 at the front ends of the arms to move radially inwardly and outwardly. It will be understood that when the distal end 50 of each tab is moved radially inwardly, the hooked ends 48 will move radially outwardly to release any instrument that happens to be engaged by the hooked ends. Referring for the moment to FIGS. 5 and 7, hooked ends 48 are shown in FIG. 5 engaged behind (proximally of) a pair of radially oppositely extending tabs 52 on the body of scope 54 having a Linvatec/Storz type of connection design. (Scope 54 is merely a diagrammatic representation of a possible type of scope usable with the invention. For clarity, light posts to communicate illuminating light to the distal end of the scope are omitted. The elongated body of the scope is also omitted. The sizes of the scopes in FIGS. 5 and 7 vary and they are shown as eyecup scopes although cartridge type endovideoscopes are equally suitable.) A circular coil spring 60 is received in recesses 62 formed in the radially outer surfaces of each lever arm 40, 42 to provide a radially inwardly directed bias to keep the hooks securely engaged with a selected instrument. Partially annular recesses 63 and 64 in the frame 45 help to retain spring 60 in place. An O-ring 66 prevents fluid leakage from the proximal end of the scope/main body assembly and O-ring 67 prevents fluid leakage at the distal end. Both locking arms must be squeezed together to release the scope and, therefore, manipulation of the device during surgery is unlikely to cause accidental scope separation from the main body. Assembly of the device does not require the arms to be pressed inwardly: the scope simply needs to be aligned with the key 44 and pushed into the main body.

Selective engagement mechanism 20 at the distal end of the main body comprises a cylindrical treaded shaft 70 having a key projection 72. Shaft 70 is adapted to be engaged by either complementarily shaped threaded nut 74a or 74b at the proximal end of either sheath 22 or bridge adapter 24, respectively (best seen in FIG. 7).

Interposed on main body 10 between its proximal and distal ends 12 and 14 is a fluid inflow, stopcock device 30 for conveying irrigating fluid from an outside source (not shown) via port 31 and fluid chamber body 32 into fluid chamber 33. Chamber body 32 is removable from main body 10 so that the interior fluid chamber 33 may be cleaned. Prior art fluid chambers are generally closed cylindrical chambers having one or more ports in a generally cylindrical surface around the fluid chamber, the ports being circumferentially spaced in a cylindrical wall joining transverse walls analogous to transverse annular walls 36a and 36b. These ports would, therefore, normally be interposed in the fluid flow path between a port such as 31 (on a removable stopcock body) and the interior of a fluid chamber. The invention has restructured the fluid chamber in a unique manner by using a process which may be termed "skeletonization". That is, opposing transverse sides of fluid chamber 33 are held together not by a pressure restricting cylindrical apertured wall as in prior art devices, but by a skeletal or framework structure which holds the opposing transverse sides together to enable components to be disassembled for cleaning while increasing fluid flow and decreasing pressure losses. In the preferred embodiment, the interior cylindrical surface 34 of body 32 defines the cylindrical outer wall of fluid chamber 33 (except for the area where port 30 intersects the cylindrical wall) and the length of chamber 32 along the axis 17 is defined by a framework of circumferentially spaced pins 35 which space the opposing transverse annular walls 36a and 36b. Body 32 may be adapted to have any number of fluid inflow stopcock ports similar to 31, fixed or rotatable, and the ports may be angled as shown or perpendicular to the axis of the main body. A pair of O-rings 37 seal the outer surface of chamber 33.

Fluid chamber 33 is defined by the combination of the core volume created by the plurality of longitudinally aligned and circumferentially arranged pins 35 retaining the proximal and distal sides 36a and 36b of the chamber together, and the surface 34 of the fluid chamber body 32. In the preferred embodiment four pins are used. The use of the pins maximizes the inlet opening and volume of the chamber to minimize any obstruction to the fluid flow from the inflow port 31 to the chamber 33. This has the beneficial effect of slowing the fluid flow down prior to its changing direction from flowing relatively transversely to the axis 17 to flowing longitudinally along the axis of the device into circular channel 38. This again minimizes pressure losses. The annular transition between the chamber 33 and the circular channel 38 at the proximal end 14 of the main body is tapered at 39 to also minimize fluid losses. It will be understood that circular channel 38 and other circular channels up and downstream from channel 38 will be necessarily made into annular channels when a cylindrical scope is inserted into the components. The principals discussed herein will, however, remain unaffected by this. The invention includes other features which enable it to have an inflow capability higher than that of prior art devices. For example, inflow port 31 has been adapted to receive a simple elastomeric tube rather than a conventional luer lock fitting which is often used. Additionally, the inflow port is angled relative to the longitudinal axis 17 to impart some distally directed momentum to the fluid to decrease the pressure (momentum) loss in the fluid flow caused by the abrupt, right angle directional flow changes imparted by many prior art inflow devices which have the inflow port perpendicularly situated relative to the longitudinal axis.

Utilizing the system as either a bridge or an arthroscopic inflow sheath provides a higher fluid flow rate than the prior art devices. Higher flow rate means a quicker response time for the associated fluid pump (not shown) to supply sufficient amount of fluid into the joint during a loss of pressure during procedures. The high flow rate of the system in the sheath mode is further facilitated by the use of the large bore inflow port 31 and large bore fluid chamber 33 within the main body as well as the large diameter sheath tube 22 and distal end fenestrations.

The body of the arthroscope sheath 22 is formed with a large diameter proximal section 80 extending for most of the length of the sheath and a smaller diameter distal section 82 adjacent the end of the sheath, section 82 having fenestrations 83. The large diameter section is sized to receive fluid from circular channel 38. A tapered transition section 84 (formed, for example, by a weld) is interposed between the large and small diameter sheath sections to facilitate insertion of the sheath into the patient. The inner diameters of the sheath sections 80, 82 and main body 10 are chosen to accommodate an arthroscope to be received within these components. The structure is different from known prior art sheaths which have a constant diameter along their entire length. It has been found that the larger diameter proximal sheath section 80 reduces pressure losses in laminar and turbulent flow and is, therefore, made as long as possible. The small diameter distal section 82 is reduced in diameter preferably only for that portion of the length of the overall sheath which is necessary to facilitate access to tight locations at the worksite. The distal end of section 72 may be angled to accommodate an angled arthroscope tip and proximal key 44 is adapted for use with an associated keyway (not shown) to properly align the various elements. While the relative lengths of the small and large diameter sheath sections may vary, in one preferred embodiment the large diameter section 80 is approximately 4 inches long while the small diameter section 82 is approximately 1 inch long. Other embodiments may be produced in which the large diameter section may be longer if the sheath must be made longer in order to provide access to worksites deeper within the body (for example, in hip arthroscopy the sheath may be made longer than in wrist arthroscopy). In general, it is preferred that the small diameter section be less than approximately 25% of the length of the sheath to achieve the beneficial high flow rates available by this design.

Figure 6:
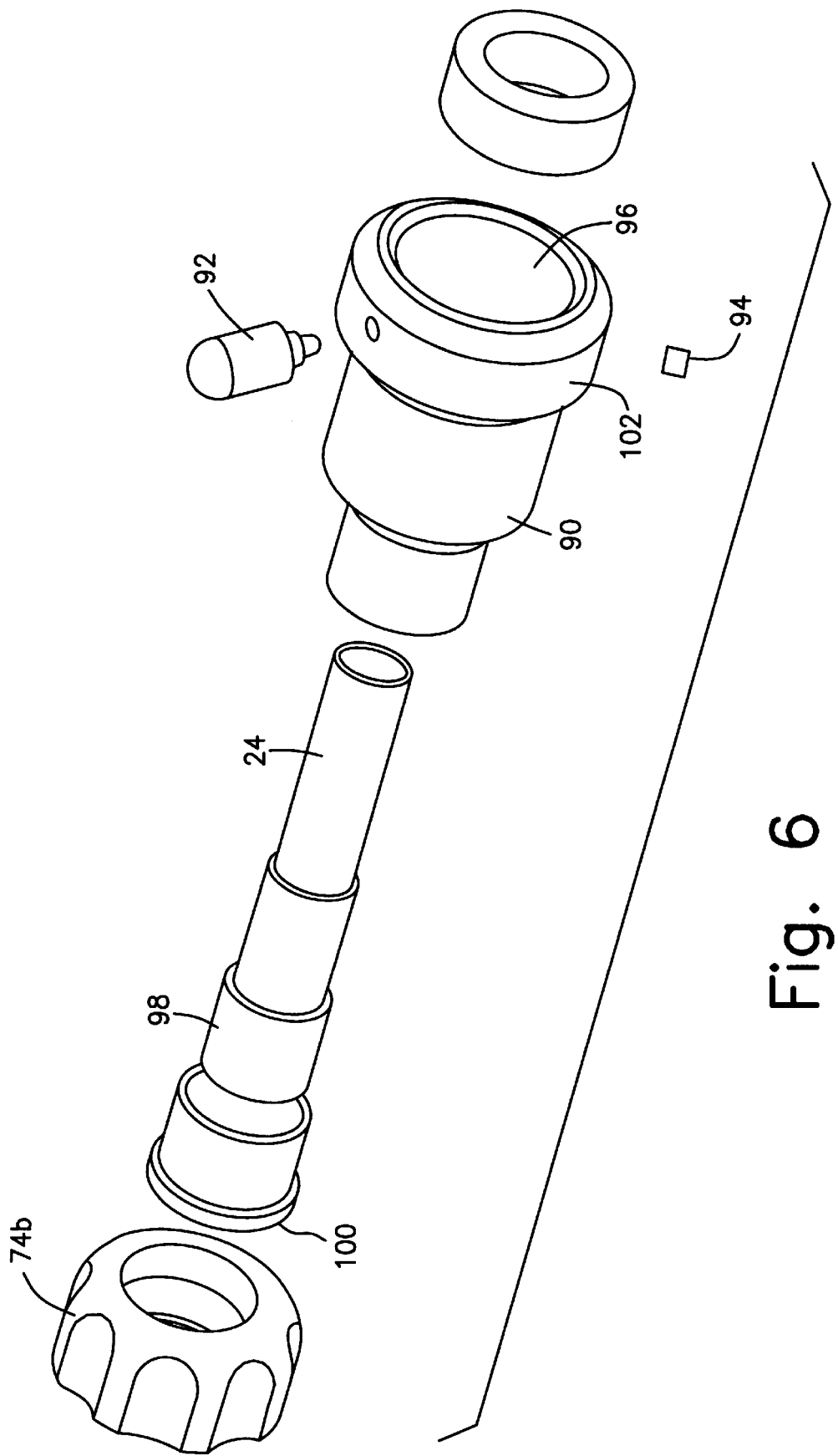
FIG. 6 is an exploded perspective view of the bridge adapter body shown in FIG. 2.

Referring to FIG. 6, bridge adapter 24 is shown in an exploded perspective view. Bridge adapter 24 comprises a mounting nut 74b at its proximal end for engaging the projection 20 extending from the main body 10. A distal body portion 90 is provided with a locking post 92 and a key pin 94 to receive selected components within the distal recess 96 of the adapter. An intermediate tubing arrangement 98 is interposed between proximal end 100 and distal end 102 and the entire assembly is attachable to the main body 10 to produce an arthroscopic bridge. Key pin 94 extends through the side wall of end 102 into recess 96 and serves to lock end 102 to selected cannulas or other instruments (not shown) having twist type or bayonet type connecting elements. The locking post 92 provides leverage in conjunction with, for example, a locking post on the instrument attached to end 102 to facilitate secure attachment of the bridge to the instrument in the proper alignment.

The modularity of the invention enables a surgeon to select (preoperatively or during surgery) whether the system should be configured as a bridge system or a scope sheath system. In a bridge system, main body 10 acts as the upper portion of the bridge and is connected to a bridge adapter 24 or lower portion as shown in FIG. 2. A bridge system allows the surgeon to connect the adapter to any one of a variety of cannulas to enable the surgeon to have multiple portal interchange of arthroscopic instruments such as shaver blades, arthroscopes, etc. through selected cannulas. In a scope sheath system, the main body 10 or upper portion of the bridge is connected to a sheath 22 as shown in FIG. 1. The sheath may then be directly inserted through a portal or a cannula. No known prior art enables the user to select a combination of components to form either a bridge system or scope system for use during a surgical procedure.

It will be understood by those skilled in the art that numerous improvements and modifications may be made to the preferred embodiment of the invention disclosed herein without departing from the spirit and scope thereof.

What is claimed is:

1. An arthroscopic system comprising:
    a first elongated instrument comprising a proximally situated first base member and a first elongated body extending axially and distally therefrom;
    a second elongated instrument comprising a proximally situated second base member and a second elongated tubular body extending axially and distally therefrom;
    a main body for joining said first instrument and second instrument, said main body having an axis, a distal end, a proximal end and an axially aligned throughbore open at both ends to receive said first elongated body therethrough, said main body comprising first connecting means at said proximal end for selective attachment to said first base member and second connecting means at said distal end for attachment to said second base member;

said first connecting means comprising:

a pair of diametrically opposed lever arms, each lever arm pivotably attached to opposing points on said main body and pivotable in a plane common to said lever arms;

spring means attached to each said lever arm to bias each said lever arm radially;

means on each said lever arm for engaging a predetermined portion of said first base member, when said first elongated body is within said throughbore, to prevent relative longitudinal motion between said first body and said main body; and said second connecting means comprising selectively detachable connection means connectable to a predetermined portion of said second base member to prevent relative longitudinal motion between said second body and said main body.

2. An arthroscopic system according to claim 1 wherein said spring means is common to both of said lever arms.

3. An arthroscopic system according to claim 2 wherein said spring means is a circular coil spring which endues and biases both lever arms simultaneously.

4. An arthroscopic system according to claim 1 wherein said throughbore comprises a distal fluid outflow channel and wherein said main body further comprises:

a fluid inlet port for communicating fluid to said throughbore, said port inclined relative to said axis at a predetermined angle;

a fluid receiving chamber axially aligned with said throughbore proximal to said distal fluid outflow channel, said fluid receiving chamber having a diameter greater than that of said throughbore; and a plurality of longitudinally aligned pins circumferentially spaced within said fluid receiving chamber at a predetermined radial distance from said axis.

5. An arthroscopic system according to claim 4 further comprising an annular tapered edge at the transition between said fluid receiving chamber and said distal fluid outflow channel.

6. An arthroscopic system according to claim 4 wherein said throughbore has a fit diameter and wherein said plurality of pins are spaced at a predetermined radial distance equal to said first diameter so that an instrument shaft having a first diameter will be able to pass.

7. An arthroscopic system according to claim 1 wherein said second instrument comprises a scope sheath, said scope sheath comprising a first longitudinally extending proximal section having a first predetermined diameter and a second longitudinally extending distal section, distal to said first longitudinally extending proximal section and having a second predetermined diameter smaller than said first diameter.

8. An arthroscopic system according to claim 7 wherein said distal section has a length less than approximately 25% the length of said proximal section.

9. An arthroscopic system according to claim 1 wherein said second instrument comprises a bridge adapter, and wherein said second elongated tubular body comprises means at its end opposite said second base member for selectively connecting thereto a predetermined third surgical instrument.

10. An arthroscopic component comprising:

a main body having an axis, a distal end, a proximal end and an axially aligned throughbore, said throughbore comprising a distal fluid outflow channel;

a fluid receiving chamber core interposed in said main body between its proximal and distal ends and axially aligned with said throughbore proximal to said distal fluid outflow channel, said fluid receiving chamber core comprising opposing transverse annular walls each having a diameter greater than that of said throughbore and spaced from each other by a plurality of longitudinally aligned, circumferentially spaced pins situated at a predetermined radial distance from said axis;

a fluid chamber body selectively attachable to said main body, said fluid chamber body comprising:

a fluid inlet port for communicating fluid to said fluid receiving chamber core; and an inwardly facing, longitudinally aligned annular wall for being situated between said opposing transverse annular walls to thereby define, in cooperation with said fluid receiving chamber core, a fluid receiving chamber.

11. An arthroscopic system comprising a first elongated instrument comprising a proximally situated first base member and a first elongated body extending axially and distally therefrom;

a second elongated instrument comprising a proximally situated second base member and a second elongated tubular body extending axially and distally therefrom;

a main body for joining said first instrument and second instrument, said main body having an axis, a distal end, a proximal end and an axially aligned throughbore open at both ends to receive said first elongated body therethrough, said main body comprising first connecting means at said proximal end for selective attachment to said first instrument and second connecting means at said distal end for attachment to said second instrument, wherein said throughbore comprises a distal fluid outflow channel and wherein said main body further comprises:

a fluid inlet port for communicating fluid to said throughbore, said port inclined relative to said axis at a predetermined angle;

a fluid receiving chamber axially aligned with said throughbore proximal to said distal fluid outflow channel, said fluid receiving chamber having a diameter greater than that of said throughbore; and a plurality of longitudinally aligned pins circumferentially spaced within said fluid receiving chamber at a predetermined radial distance from said axis.

* * * * *